US00PP25729P2

(12) United States Plant Patent
Trees

(10) Patent No.: US PP25,729 P2
(45) Date of Patent: Jul. 21, 2015

(54) ***BUDDLEJA* PLANT NAMED 'BOSEDAZE'**

(50) Latin Name: ***Buddleja* hybrid**
Varietal Denomination: Bosedaze

(71) Applicant: Ball Horticultural Company, West Chicago, IL (US)

(72) Inventor: Scott Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 149 days.

(21) Appl. No.: 13/998,153

(22) Filed: Oct. 7, 2013

(51) Int. Cl.
*A01H 5/02* (2006.01)

(52) U.S. Cl.
USPC ..... Plt./242

(58) Field of Classification Search
USPC ..... Plt./242
See application file for complete search history.

*Primary Examiner* — Anne Grunberg
(74) *Attorney, Agent, or Firm* — Audrey Charles

(57) ABSTRACT

A new and distinct cultivar of *Buddleja* plant named 'Bosedaze', characterized by its dark red-purple colored flowers, dark green-colored foliage, and moderately vigorous, upright growth habit, is disclosed.

2 Drawing Sheets

Latin name of genus and species of plant claimed: *Buddleja* hybrid.

Variety denomination: 'Bosedaze'.

BACKGROUND OF THE INVENTION

The present invention relates to a new and distinct cultivar of *Buddleja* plant botanically known as *Buddleja* hybrid and hereinafter referred to by the cultivar name 'Bosedaze'.

The new cultivar originated in a controlled breeding program in Guadalupe, Calif. during September 2011. The objective of the breeding program was the development of *Buddleja* having distinctive flower coloration, good repeat blooming, and well-branched habits.

The new *Buddleja* cultivar is the result of cross-pollination. The female (seed) parent of the new cultivar is 'Attraction', not patented, characterized by its dark red-purple colored flowers, medium green-colored foliage, and moderately vigorous, upright growth habit. The male (pollen) parent of the new cultivar is 'Miss Ruby', U.S. Plant Pat. No. 19,950, characterized by its dark red-purple colored flowers, medium green-colored foliage, and moderately vigorous, compact-upright growth habit. The new cultivar was discovered and selected as a single flowering plant within the progeny of the above stated cross-pollination during August 2012 in a controlled environment in Guadalupe, Calif.

Asexual reproduction of the new cultivar by terminal stem cuttings since August 2012 in Guadalupe, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Bosedaze' as a new and distinct cultivar of *Buddleja* plant:

1. Dark red-purple colored flowers;
2. Dark green-colored foliage; and
3. Moderately vigorous, upright growth habit.

Plants of the new cultivar differ from plants of the female parent in having smaller inflorescences and a more compact habit.

Of the many commercially available *Buddleja* cultivars, the most similar in comparison to the new cultivar is the male parent 'Miss Ruby', U.S. Plant Pat. No. 19,950. However, in side by side comparisons, plants of the new cultivar differ from plants of 'Miss Ruby' in at least the following characteristics:

1. Plants of the new cultivar have larger leaves than plants of 'Miss Ruby'; and
2. Plants of the new cultivar have larger inflorescences than plants of 'Miss Ruby'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Bosedaze'. The plants were grown in one-gallon containers for 6 months in an outdoor nursery in Guadalupe, Calif. Plants were pinched at transplant and within two months after transplant. In early June 2013, the plants were transplanted to field conditions in West Chicago, Ill.

DETAILED BOTANICAL DESCRIPTION

Figure 1:
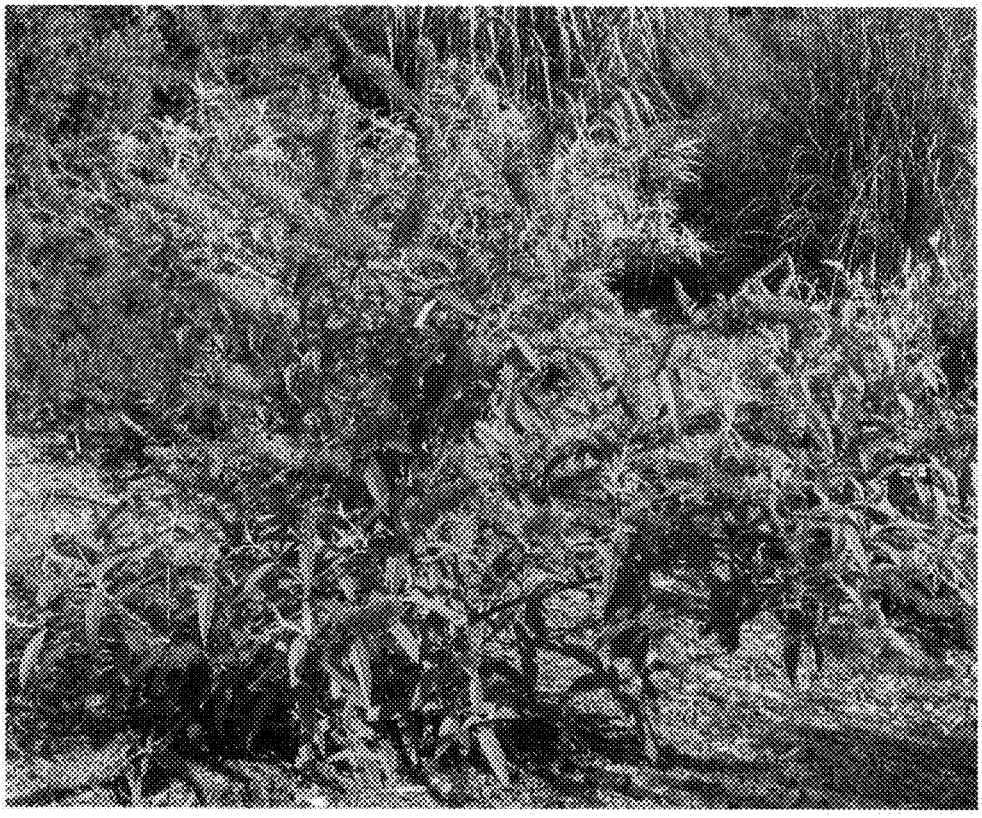
FIG. 1 illustrates a side view of the overall growth and flowering habit of 'Bosedaze'.
Figure 2:
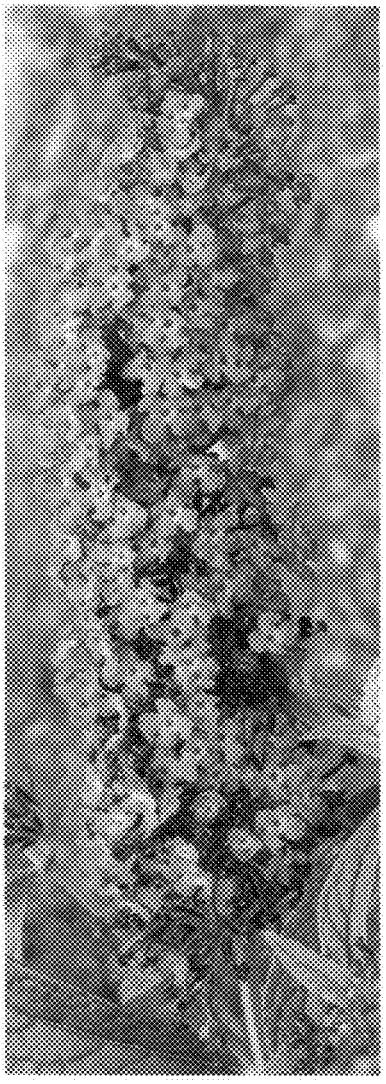
FIG. 2 illustrates a close-up view of an individual inflorescence of 'Bosedaze'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in August 2013 under natural light conditions in West Chicago, Ill.

The following descriptions and measurements describe plants produced from cuttings from stock plants and grown in a glass-covered greenhouse for two months under conditions comparable to those used in commercial practice. The plants were transplanted and grown for 6 months in one-gallon containers in an outdoor nursery in Guadalupe, Calif. Plants were pinched at transplant and within two months after transplant. In early June 2013, the plants were transplanted to field conditions in West Chicago, Ill. where outdoor temperatures ranged from 88° F. to 67° F. (31° C. to 19° C.) during the day and approximately 74° F. to 41° F. (23° C. to 5° C.) during the night. Measurements and numerical values represent averages of typical plants.

Botanical classification: *Buddleja* hybrid cultivar Bosedaze.

Parentage:

*Female parent*.—'Attraction', not patented.

*Male parent*.—'Miss Ruby', U.S. Plant Pat. No. 19,950.

Propagation:

*Type cutting*.—Terminal stem.

*Time to initiate roots*.—Approximately 14 to 20 days.

*Time to produce a rooted cutting*.—Approximately 12 to 16 weeks.

*Root description*.—Fine, fibrous white to brown in color.

*Rooting habit*.—Freely branching, moderately dense.

Plant description:

*Commercial crop time*.—Approximately 3 to 4 months from a rooted cutting to finish in a one-gallon container.

*Growth habit and general appearance*.—Moderately vigorous, upright.

*Size*. —Height from soil level to top of plant plane: Approximately 89.0 cm. Width: Approximately 132.0 cm.

Branching habit.—Freely branching. Pinching enhances lateral branching. Quantity of branches per plant: Approximately 3 main branches with 6 to 8 laterals on each main branch.

*Lateral branch*.—Shape: Square becoming round with age. Strength: Strong. Length to base of inflorescence: Approximately 19.5 cm. Diameter: Approximately 5.0 mm. Length of central internode: Approximately 4.0 cm. Texture of young branches: Densely pubescent with stellate hairs. Texture of mature branches: Densely pubescent with stellate hairs, base becomes glabrous with age. Color of young stems: 146B with pubescence of NN155A. Color of mature stems: 146B and N199B with pubescence of NN155A.

Foliage description:

*General description*.—Quantity of leaves per branch: Approximately 8. Fragrance: None detected. Form: Simple. Arrangement: Opposite.

*Leaves*.—Aspect: Primarily perpendicular to stem. Shape: Narrowly elliptical. Margin: Serrulate. Apex: Acute. Base: Broadly attenuate. Venation pattern: Pinnate, reticulate. Length of mature leaf: Approximately 10.5 cm. Width of mature leaf: Approximately 2.7 cm. Texture of upper surface: Sparsely pubescent with glands. Texture of lower surface: Densely pubescent with lanulose hairs. Color of upper surface of young foliage: 137A with indistinguishable venation. Color of lower surface of young foliage: 191B with venation of 194B. Color of upper surface of mature foliage: Darker than 137A with indistinguishable venation. Color of lower surface of mature foliage: 191B with venation of 147C.

*Petiole*.—Length: Approximately 3.0 mm. Diameter: Approximately 1.5 mm. Texture: Densely pubescent with lanulose hairs. Color: 147C.

Flowering description:

*Flowering habit*.—'Bosedaze' is freely flowering under outdoor growing conditions blooming from late spring through mid-fall.

*Lastingness of individual flower*.—Approximately 5 to 7 days.

Inflorescence description:

*General description*.—Type: Terminal panicles, each panicle having about 2 to 4 branches. Flowers persistent, facing upward and outward. Quantity of open inflorescences per plant: Approximately 33. Fragrance: Slightly sweet. Depth or height of inflorescence: Approximately 15.0 cm. Width: Approximately 5.0 cm. Quantity of flowers per inflorescence: Approximately 250, opening from base to apex.

*Rachis*.—Strength: Strong. Length: Approximately 17.5 cm. Diameter: Approximately 2.5 mm. Texture: Densely pubescent with stellate hairs. Color: 146B with pubescence of NN155A.

Flower description:

*Type*.—Single, salverform.

*Bud just before opening*.—Shape: Oblong. Length: Approximately 6.0 mm. Diameter: Approximately 1.0 mm. Texture: Moderately pubescent. Color of petals: 77A.

*Corolla*.—Shape: Rotate, 4 petals arranged in a single whorl. Depth: Approximately 1.1 cm. Width: Approximately 7.0 mm.

*Petals*.—Shape: Rotund. Margin: Erosulate. Apex: Rounded. Length from throat: Approximately 3.0 mm. Width: Approximately 3.0 mm. Texture of upper and lower surfaces: Glabrous. Color of upper surface when first and fully open: 72B with 72C at base. Color of lower surface when first and fully open: 72C.

*Corolla tube*.—Length: Approximately 1.0 cm. Width: Approximately 1.0 mm. Diameter of throat opening: Approximately 1.0 mm. Texture of inner surface: Moderately pubescent. Texture of outer surface: Glabrous. Color of inner surface: 17A with 15A at throat opening. Color of outer surface: 72C with a faint tint of 53A.

*Calyx*.—Shape: Tubular. Length: Approximately 3.0 mm. Diameter: approximately 1.0 mm.

*Sepals*.—Quantity per flower: 4, fused at base. Apex: Acute. Margin of free portion: Entire. Length: Approximately 3.0 mm. Width: Less than 1.0 mm. Texture of inner surface: Glabrous. Texture of outer surface: Moderately pubescent. Color of inner surface: 137A. Color of outer surface: 137B and pubescence of NN155A.

*Pedicels*.—Strength: Strong, flexible. Length: Approximately 1.0 mm. Diameter: Approximately 1.0 mm. Texture: Densely pubescent with stellate hairs. Color: 137B with pubescence of NN155A.

*Reproductive organs*.—Androecium: Stamen quantity: 4 per flower, completely adnate to corolla. Anther shape: Lanceolate. Anther length: Approximately 1.0 mm. Anther color: 158D. Pollen amount: Sparse. Pollen color: NN155A. Gynoecium: Pistil quantity: 1 per flower. Pistil length: Approximately 4.0 mm. Stigma shape: Cleft, two-parted. Stigma length: Approximately 1.0 mm. Stigma color: Closest to 144B. Style length: Approximately 1.0 mm. Style color: Closest to 145D, opaque. Ovary length: Approximately 2.0 mm. Ovary color: Closest to 144B.

Seed and fruit production: Neither seed nor fruit production has been observed.

Disease and pest resistance: Resistance to pathogens and pests common to *Buddleja* has not been observed.

What is claimed is:

1. A new and distinct cultivar of *Buddleja* plant named 'Bosedaze', substantially as herein illustrated and described.

* * * * *